United States Patent [19]

Leibinger et al.

[11] Patent Number: 4,587,963
[45] Date of Patent: May 13, 1986

[54] INSTRUMENT FOR POSITIONING A CERCLAGE FIXATION DEVICE AROUND FRACTURED BONE PARTS

[76] Inventors: Karl Leibinger; Franz Leibinger, both of Josef-Lang. Str. 22, 7202 Mulheim 2, Fed. Rep. of Germany

[21] Appl. No.: 613,030

[22] Filed: May 22, 1984

[30] Foreign Application Priority Data

May 26, 1983 [DE] Fed. Rep. of Germany ....... 3319149

[51] Int. Cl.⁴ .............................................. A61F 5/04
[52] U.S. Cl. ................................. 128/92 B; 128/92 E; 128/91 A
[58] Field of Search ................. 128/92 R, 92 E, 92 B, 128/92 ED, 92 G, 91 A, 303 R, 309, 326, 92 EA

[56] References Cited

U.S. PATENT DOCUMENTS

| | | | |
|---|---|---|---|
| 914,182 | 3/1909 | Pfeffer | 128/92 ED |
| 1,304,620 | 5/1919 | Steinkoenig | 128/92 E |
| 1,641,077 | 8/1927 | Fouquet | 128/92 E |
| 3,670,411 | 6/1972 | Peters | 128/92 R |
| 4,050,464 | 9/1977 | Hall | 128/92 E |
| 4,456,006 | 6/1984 | Wevers et al. | 128/92 B |
| 4,473,068 | 9/1984 | Oh | 128/92 R |
| 4,512,346 | 4/1985 | Lemole | 128/92 B |
| 4,527,554 | 7/1985 | Klein | 128/92 E |

FOREIGN PATENT DOCUMENTS

| | | | |
|---|---|---|---|
| 825049 | 5/1981 | U.S.S.R. | 128/92 E |
| 995769 | 2/1983 | U.S.S.R. | 128/92 EA |

OTHER PUBLICATIONS

Down Bros. and Mayer & Phelps, Ltd., p. G67 of the 20th Ed. Catalog.
Murray-Baumgartner Surg. Inst. Co., p. 90, Catalog of 1934.

Primary Examiner—Robert Peshock
Assistant Examiner—C. W. Shedd
Attorney, Agent, or Firm—Thomas P. Mahoney

[57] ABSTRACT

To hold mating bone parts or sections together during osteosynthesis, the ends of a piece of wire for holding the bone parts together are passed through narrow boreholes of one or more plates and are deformed at that section to retain them in the boreholes. The wire is subjected by means of tightening means to a desired tractive force and is deformed by means of deformation means. The tightening means and the deformation means cooperate to place the wire under traction and deform the same where it issues from the boreholes in the plate or plates. The deformation means operate like pliers in which the tightening means is located. The tightening means incorporates a shaft which can be driven with an adjustable torque and, by means of a freewheeling coupling, the shaft is mounted in a manner so that it can be rotated only in one direction.

15 Claims, 6 Drawing Figures

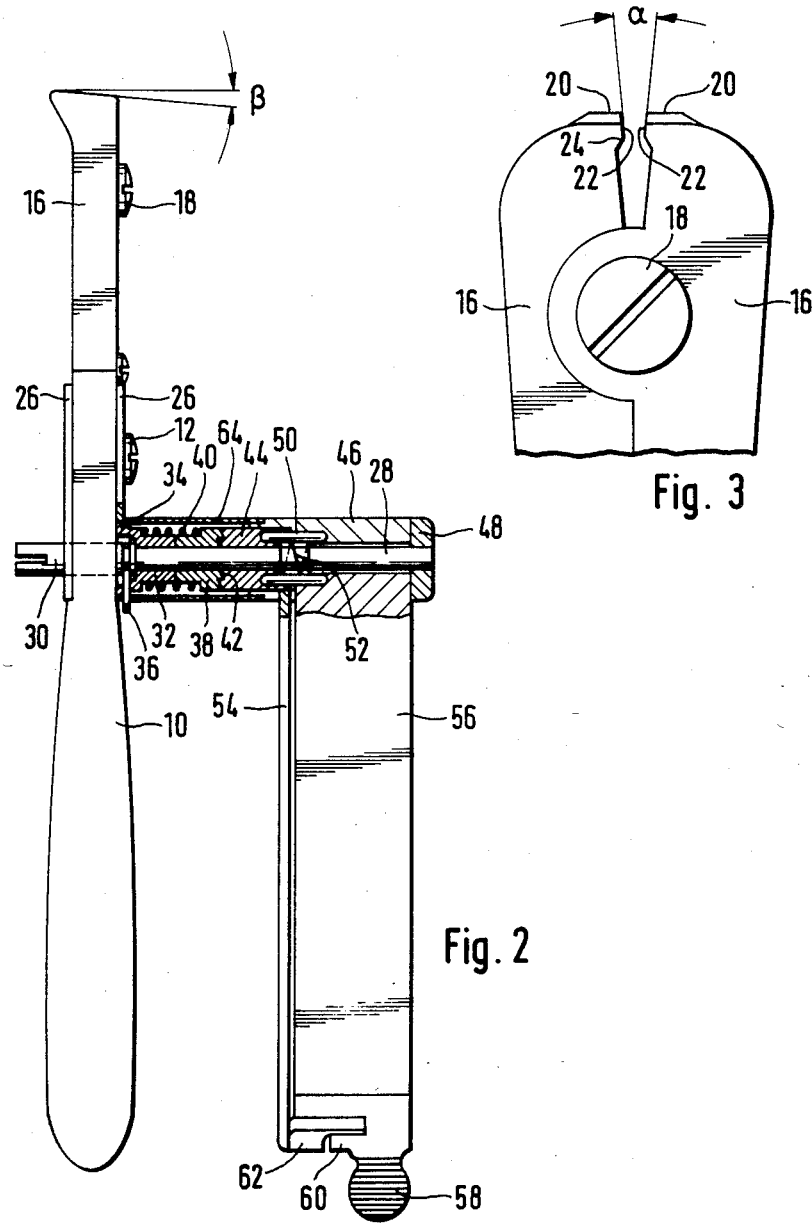

INSTRUMENT FOR POSITIONING A CERCLAGE FIXATION DEVICE AROUND FRACTURED BONE PARTS

BACKGROUND OF THE INVENTION

The invention relates to an instrument for the mutual position-fixtation of bone parts or sections during osteosynthesis. In surgical and orthopedic operative techniques it is frequently necessary to fix bone parts, which have been separated through surgical means or through a fracture, in an exact mutual position and to join them together under pressure. For such so-called osteosynthesis it is common to retain the bone parts to be joined together by means of metal splints which are preferably screwed to the bone parts. The affixation of the splints by means of screws frequently results in further damage to the bone. Furthermore, the splints can also cause irritation and infections.

In the course of osteosynthesis of bones which are divided in a longitudinal direction, in particular, for example, in the case of the sternum which is separated in a longitudinal direction for cardiac surgery, it is known to place wire loops around the bone parts and to twist the wire ends together, so that the wire loops come to lie under tractive force around the bone parts and hold the same together. When twisting the wire ends together, the created tractive force of the wire can be determined only by feel and therefore only very inaccurately.

A tractive force whish is of a too low order of magnitude does not hold the bone parts together under sufficient pressure, which is disadvantageous for the process of osteosynthesis. However, when the wire ends are twisted together too tightly, a buckling-type fracture of the wire can occur. If this type of fracture occurs during the surgical procedure, this entails an unfavorable prolongation of the duration of the surgery. However, such buckling-type fractures also manifest themselves only after the conclusion of the surgery, which is particularly unfavorable, since the surgical wound has to be reopened in order to insert a new wire loop. Finally, the twisted wire ends can lead to tissue irritations which could disturb and prevent the healing process.

OBJECTS AND ADVANTAGES OF THE INVENTION

The invention places at one's disposal a device for the mutual position-fixation of bone parts, making it possible for the bone parts to be reliably held together under a specific tractive force while preventing breaking of the wire during or after surgery.

For the purpose of the mutual position-fixation of the bone parts to be joined together, a wire—in loop form—is guided around the bone parts to be held together in accordance with the invention. The two ends of the wire loop are guided through narrow boreholes of a metallic plate, whereby the borehole diameters are only slightly larger than the wire diameter. In actual practice, a diameter difference of a maximum of 0.08 mm, preferably one of 0.03 to 0.05 mm, has been effective.

The wire is deformed directly at the plate by the device of the invention so that the wire ends can no longer slip through the boreholes of the plate. First of all, one wire end is secured in this manner, then, by means of a tightening device, a tractive force is executed with respect to the other wire end until the required tension of the wire loop is attained and, finally, the second wire end is deformed directly at the plate by the device, namely, in such a manner so that the wire end is tightly retained by the plate.

In other cases of application, the bone parts which are to be held together are drilled through and a wire is passed through the bone parts. The one end of the wire is retained in the borehole of a plate through deformation in the described manner. The diametrically arranged other wire end is guided through a borehole of an additional plate and is then tightened to the desired tractive force by means of the device and is then deformed, so that the wire is retained in the plate under the desired tractive force.

Investigations have shown that, at a customary wire diameter of, for example, 1.0 mm, a tractive force of more than 50 kp can be exerted on the wire ends which are retained in the perforated plate, without the deformed wire end being pulled through the borehole of the plate. Such high tractive forces cannot be attained in the course of the conventional twisting of the wire ends, since the tensile load capacity of the wire is reduced by the buckling load during the twisting procedure.

A further advantage results from the fact that the wire ends can be cut off directly adjacent the deformations, so that practically no protruding wire ends are present to cause tissue irritations which delay the healing process.

In a particularly advantageous form of the device of the invention the tightening and deformation functions are united in one instrument. The wire, which has been pulled through the boreholes of the plate, can be tightened with the instrument to the desired tractive force, and the end of the wire which is under this tractive force can be deformed directly at the plate.

In an expedient manner, the deformation function is accomplished by jaws which bluntly abut against one another with flat surfaces at their frontal end. The flat surfaces permit the achievement of high deforming power when the operating surgeon has to use great force.

The surfaces of the jaws which abut against one another in the closed state preferably touch one another only along a line which is spaced a distance from the frontal edge of the jaws. In the closed state of the jaws, the two surfaces abutting against one another form an outwardly opening angle. Along the contact line of the jaws, the wire, under suitable pressure application, is squeezed to such an extent that a shear point is created. The surfaces of the jaws which diverge outwardly from one another guarantee that in the area lying between the plate and the shear point the wire is deformed to a sufficiently high degree, but is not cut off.

The tightening means of the instrument is preferably designed as a shaft onto which the wire end is wound. The shaft is mounted, in a rotatable manner, in the deformation means which, for purposes of tightening the wire, braces itself at the plate. The deformation means supports itself with the frontal edges of the jaws at the plate, so that the above-explained deformation position and the assigned shear point result automatically.

In order to be able to wind the wire on the shaft for the generation of the tractive force, without which the shaft under the effect of the tractive force rotates backwardly, a freewheeling coupling is provided which permits rotation of the shaft only in one direction of rotation.

In order to attain an accurately defined tractive force on the wire, means for the limitation and the determination of the moment of rotation for the drive of the shaft are provided. In a simple form, a leaf-type spring projecting radially from the shaft is provided, which serves as driving element for the shaft. Depending on the magnitude of the amount of rotation expended for the drive of the shaft, the free end of the leaf-type spring becomes deflected so that the deflection of the leaf-type spring, which can be read off on a scale, can be taken as a measure of the tractive force exerted on the wire.

In order for the driving leaf-type spring not to intrude on the surgical area during the rotation of the shaft, the leaf-type spring preferably engages with the shaft through the intervention of a ratchet gear, so that pivoting of the radially projecting leaf-type spring is necessary only over a small angular range.

Other objects and advantages of the invention will be apparent from the following specification and the accompanying drawings which are for the purpose of illustration only.

BRIEF DESCRIPTION OF THE DRAWINGS

FIG. 2 is a side elevational view of the instrument, partially shown in axial cross section;

FIG. 3 shows the jaws of the instrument;

DESCRIPTION OF A PREFERRED EMBODIMENT

Figure 1:
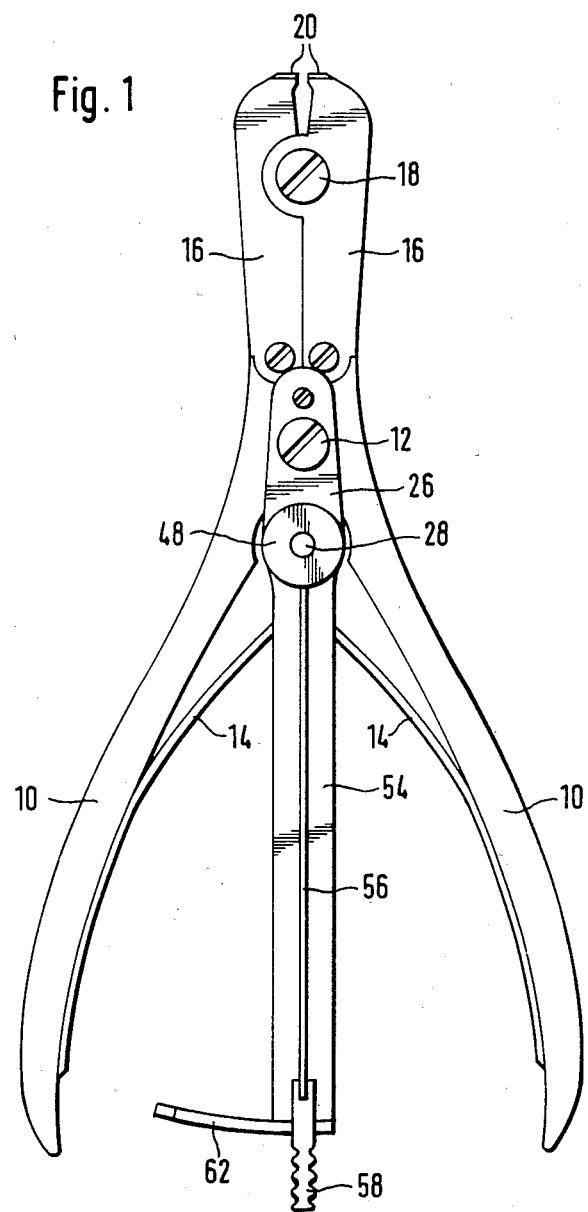
FIG. 1 is a front elevation view of the instrument which combines the tightening and deformation means.

In the drawings, only the instrument is illustrated, in which the tightening means and the deformation means are combined. As previously indicated, the wire acts to hold the plate, which serves as a splint, in a predetermined relationship with the bone sections or parts.

The instrument incorporating the tightening means and the deforming means is constructed in the form of pliers. The pliers incorporate two hand levers 10 which, in opposition to the force of two leaf-type springs, can be pressed together around a pivotal axis 12. The short front ends of the hand levers 10 engage in an articulate manner with the rear longer arms of jaws 16, which are designed as two-armed levers, which can be pivoted with respect to each other around a pivotal axis 18. The lever relationships of the hand levers 10 and of the jaws 16 achieve a high power ratio, so that the frontal ends of the jaws 16 are pressed against one another with great force when the hand levers 10 are pressed together.

During the closing of the pliers, the outer ends 20 of the jaws 16 bluntly abut against one another with flat angularly oriented surfaces 22. FIG. 3 clearly shows that the flat surfaces 22 of the outer ends 20 of the jaws 16 form an angle $\alpha$ in the closed state. Thus, the surfaces 22, during the closing of the pliers, engage each other only along a line 24 and toward the outer ends 20 diverge from one another by the angle $\alpha$.

In the area of the outer ends 20, the jaws are extended in one direction beyond the pivotal plane, as shown in FIG. 2. As also can be seen from FIG. 2, the outer ends 20 are inclined at an angle $\beta$ in direction toward their closing slit, so that they display the greatest distance from the pivotal axes 18 or 12 at the side projecting beyond the pivotal plane. The opening angle $\alpha$ of the angle surfaces 22 preferably amounts to about 12°, whereas the angle of inclination $\beta$ preferably amounts to about 5°.

By means of the pivotal axis 12, base plates 26 are mounted on each side of the hand levers 10. Within these base plates 26 a shaft 28 is mounted in a rotatable manner, which is arranged between the hand levers 10 in perpendicular manner to the pivotal plane of the same. One extremity of shaft 28 extends beyond the pivotal plane of the hand levers 10 in the same direction and in essence by the same amount as the extension of the outer ends 20 of the jaws 16, as can be seen from FIG. 2. This extremity of shaft 28 incorporates an axial slit 30 for receiving one end of the aforementioned wire.

The other extremity of shaft 28 which projects beyond the opposite side of the pivotal plane of the hand levers 10 is rotatably mounted in a bushing 32. By means of axially projecting lugs 34, the bushing 32 engages with corresponding recessed areas of the base plate 26, so that it is retained against rotation with respect to the base plate 26, and thereby with respect to the pliers. A U-shaped wire spring 36 is inserted in bushing 32 and elastically engages a circumferential groove of the shaft 28 with its legs and retains the same axially with respect to the base plates 26 and thereby with respect to the pliers.

A bushing 38 encompasses the shaft 28 in a rotation-resistant manner and adjoins bushing 32. A spiral spring 40, in a tightly fitting manner, coaxially encompasses the bushings 32 and 38. The spiral spring 40 is inserted in an axial direction between one radial shoulder each of bushings 32 and 38, so that it cannot expand in an axial direction. Through the spiral spring 40, a freewheeling coupling is formed between the bushing 38 and the shaft 28 which is connected with the same in a rotation-resistant manner, and the bushing 32 or the pliers. When the bushing 38 is rotated in a clockwise direction (FIG. 1), the rotation is transferred to the spiral spring 40 which expands slightly in the radial direction. The bushing 38 and therewith the shaft 28 can freely rotate clockwise. However, when the bushing 38 is rotated in the opposite direction of rotation (in FIG. 1 counterclockwise), then the spiral spring 40 is reduced in diameter. Thus, the spiral spring 40 tightly clamps itself on the bushing 32 and on the bushing 38, so that the bushing 38 is tightly retained against rotation with respect to the bushing 32. Consequently, rotation of the bushing 38 and therewith of the shaft 28 in this direction (namely, the counterclockwise direction as indicated in FIG. 1) is also not possible.

On the extremity facing away from the bushing 32, the bushing 38 incorporates a ratchet-type gear 42. The ratchet-type gear 42 engages a corresponding ratchet-type gear at the rear end of an axially adjoining third bushing 44, which in a freely rotatable manner is mounted on shaft 28. The end of the shaft 28, in a freely rotatable manner, penetrates a cylindrical block 46 which axially adjoins the bushing 44. A disc 48 is mounted in a rotation-resistant manner on shaft 28 and axially supports the cylindrical block 46. With respect to the cylindrical block 46, the bushing 44 is rotation-resistant, but is axially displaceable along shaft 28. Two guide pins 50 serve for this purpose, which pins 50 are inserted into the blind boreholes of the bushing 44 and the cylindrical block 46 adjacent surfaces. A compression spring 52, which is inserted between the adjacent surfaces of the bushing 44 and of the cylindrical block 46, presses the bushing 44 axially against the bushing 38, so that the ratchet gears 42 of said bushings 44 and 38 engage with each other. A covering sleeve 64 protects the bushings 32, 38 and 44, as well as the spiral spring 40 and the ratchet gears 42 from dirt which could penetrate the same.

The cylindrical block 46 incorporates a radially projecting arm 54, and a leaf-type spring 56 is mounted on the cylindrical block 46 parallel to the arm 54. In the tension-free state, the leaf-type spring 56 projects in the same radial direction as the arm 54, as shown in FIGS. 1 and 2. At the free end of the leaf-type spring 56, a handle 58 is affixed by means of which the leaf-type spring can be pivoted. A pointer 60, which is provided on the handle 58, moves along a scale 62 which projects in a circumferential direction from the end of the arm 54.

When the cylindrical block 46 is rotated by means of the leaf-type spring 56 in the clockwise direction, FIG. 1, the cylindrical block 46, through the intervention of the guide pins 50, rotates the bushing 44. The compression spring 52 urges the ratchet gears 42 into gear, so that the bushing 44 also rotates the bushing 38 and the shaft 28 which, in a rotation-resistant manner, is connected with the same. The freewheeling coupling which is created by the spiral spring 40 allows the rotation of the bushing 38 and the shaft 28 in the clockwise direction.

However, if the cylindrical block 46 is rotated counterclockwise by means of the leaf spring 56, the bushing 44 is also rotated by means of the guide pins 50. The bushing 44 tries to rotate the bushing 38 clockwise by means of the ratchet gears 42. However, the spiral spring 40 prevents the bushing 38 counterclockwise rotation and the ratchet gears 42 disengage in opposition to the pressure of the compression spring 42. Consequently, while the shaft 28 is immoblized, the cylindrical block 46 and the bushing 44 can be freely rotated counterclockwise by means of the leaf-type spring 56.

In utilizing the instrument the one end of the wire, through which the bone parts are to be held together, is passed through the borehole of the plate, the diameter of the borehole being only slightly larger than the wire diameter. By means of the flat inclined surfaces 22 of the jaws 16, the cross section of the wire end is deformed so that it can no longer be pulled through the borehole of the plate.

Subsequently, the other wire end is either placed around the bone parts which are to be held together and passed through a second borehole in the plate, or the wire is pulled through a hole which has been drilled into the bone and passed through a corresponding borehole in a diametrically arranged second plate.

The free end of the wire is then inserted into the slit 30 of shaft 28. The pliers, by means of the frontal ends 20 of the jaws 16, are braced in such a manner on the plate that the plate borehole and the wire which had been pulled through this borehole are located between the jaws 16. The shaft 28 is then rotated by means of the leaf-type spring 56, whereby the wire is wound onto the shaft 28. The freewheeling coupling created by the spiral spring 40 permits free rotation of the shaft 28 so that the wire cannot become unwound again. The ratchet-type locking mechanism formed by the ratchet gears 42 permits the leaf-type spring 56 to be pivoted only through a certain angle to rotate the shaft 28 and for a subsequent use to be pivoted back again. As a result, it is possible to pivot the leaf-type spring 56, for example, only within the area of the hand levers 10. A complete rotation of the leaf-type spring 56, in the course of which the latter should intrude upon the surgical area, is not necessary.

As soon as the wire has become taut during the rotation of the shaft 28, a torque has to be applied to the shaft 28 in order to tighten the wire. This torque, which corresponds to the tractive force imposed on the wire, can be determined by the deflection of the leaf-type spring 56 and can be accurately read off on the scale 62 by means of the pointer 60, namely, when the leaf-type spring 56 is pivoted by means of the handle 58.

As soon as the tractive force, which is required to hold the bone parts together, is attained for the optimum osteosynthesis, the hand levers 10 are pressed together, as a result of which the jaws 16 close. Thereby, the flat inclined surfaces 22 of the frontal ends 20 of the jaws 16 are pivoted toward one another and deform the wire cross section to such an extent that the wire end can no longer slip back through the borehole in the plate. The aperture angle $\alpha$ of the surfaces 22 insures that the squeezing of the wire is of the greatest order of magnitude along the shear line 24. Thus, by the contact line 24 a shear line is created in the wire adjacent the deformation area. In the course of a subsequent further tightening of the wire by means of the leaf-type spring 56, the wire then breaks at the shear line.

The freewheeling coupling of the shaft 28 insures, also at the time of deformation, that the wire is held at the adjusted tractive force.

The inclination of the frontal ends 20 of the jaws 16 by the angle $\alpha$ insures that, during the tightening of the wire, the plate together with the wire cannot slip away from the frontal ends 20 of the jaws 16. If the plate does slip, this can only take place in direction of the angle. Consequently, the plate can move only in that direction and the wire moves toward the jaws 16. Therewith, slippage from the plate of the frontal ends 20 of the jaws 16 bracing themselves on the plate is prevented and, likewise, disengagement of the wire from the shaft 28 is prevented.

Figure 4:
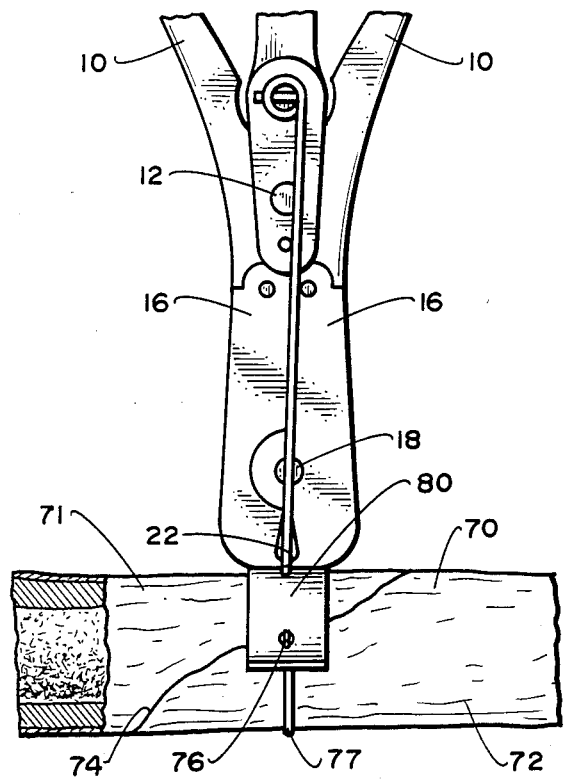
FIG. 4 is a side elevational view illustrating the operation of the instrument on a fractured bone.
Figure 5:
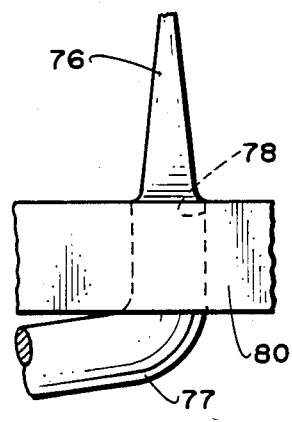
FIG. 5 is an enlarged fragmentary end elevational view showing the deformed wire end.
Figure 6:
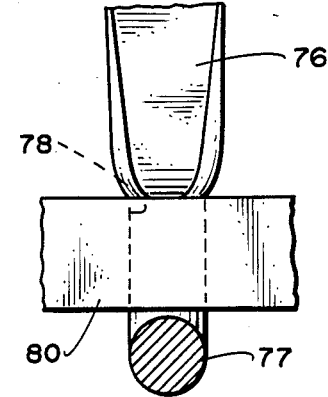
FIG. 6 is a side elevational view similar to FIG. 5.

Shown in FIGS. 4–6 of the drawings is the manner in which the two ends 70 and 71 of the fractured bone 72 are maintained in operative and healing relationship with each other by the use of the instrument of the invention. The fracture line is shown at 74, and the wire 76 is disclosed as partially encompassing the two ends 70 and 71 of the bone 72 and having its deformed ends 76 juxtaposed to the bores 78 in the plate 80.

As previously indicated, while the wire 76 is under tension, the last deformed extremity 76 is provided on the wire by the instrument, thus compressing the extremities 70 and 71 of the bone 72 toward each other. The deformed extremities 76 of the wire prevent the wire 77 from being drawn through the bores 78 in the plate 80 and cause the wire 77 to maintain its tension on the bone ends 70 and 71.

Thus, the adjacent ends of the fractured bone are held securely in place by the tension exerted by the wire 76 on the plate 80 and the deformed extremities 76 of the wire protrude a minimal amount into the adjacent tissue or musculature.

We claim:
1. In an instrument for the mutual positioning and fixtation of adjacent bone parts by means of a wire which holds the bone parts together by a tractive force, said wire being threaded through boreholes in a plate disposed in contiguity to said bone parts, said boreholes having a diameter which is only slightly larger than the diameter of said wire, the combination of: deformation means on said instrument engageable with one end of said wire for deforming the cross section of said wire sufficiently to prevent said one end from being pulled through the associated borehole; and traction means on said instrument engageable with the other end of said wire after it has been threaded through the other of said boreholes to impose a tractive load on said wire, said deformation means being operable on the other end of said wire immediately adjacent said other borehole to deform the cross section of said wire and to prevent said other end of said wire from being pulled through its borehole and thereby to maintain the tractive load of said wire against the mutually positioned bone parts.

2. The instrument of claim 1 in which said deformation means includes wire scoring means for reducing the cross section of said wire adjacent the deformed areas thereof to a minimum sufficient to permit the facile removal of the remaining portions of the ends of said wire adjacent said deformations.

3. The instrument of claim 1 in which said traction means includes wire gripping means and actuating means for causing a tractive load to be imposed upon said wire.

4. The instrument of claim 3 in which said actuating means for said wire gripping means includes a uni-directional overrunning drive for maintaining the traction on the other end of said wire during the deformation of the other end of said wire by said instrument.

5. The instrument of claim 1 in which said deformation means includes lever actuated jaws having inclined deformation surfaces which terminate inwardly in scoring surfaces engageable with said wire after the cross section thereof has been deformed by said inclined surfaces.

6. In an instrument for securing the adjacent extremities of bone parts in mutual positions by the use of at least one plate disposed in contiguity to one or both of said parts, said plate having boreholes therein, and a wire engageable with said bone parts to maintain traction on said bone parts urging them toward said plate, said plate having boreholes therein of a diameter slightly greater than the diameter of said wire, the combination of: deformation means on said instrument for deforming the cross section of one end of said wire after it has been inserted through one of said boreholes and into engagement with said bone parts, said deformation means including jaws having outwardly inclined flat deformation surfaces and being engageable with each other at the inner ends of said surfaces so that the closing of said jaws will cause the deformation of the cross section of said wire at said one end thereof to prevent said one end from being drawn through the associated borehole and so that the abutting inner extremities of said surfaces will form a score line immediately adjacent the deformed portion of the cross section of said one end of said wire; and tightening means for drawing the other end of said wire through the associated borehole to impose a tractive load upon said wire, said tractive load being imposed on said bone parts while said deformation means deforms said other end of said wire to prevent said other end of said wire from being pulled through its borehole and thereby to maintain said tractive load thereof upon said bone parts.

7. The instrument of claim 6 in which said tightening means is engageable with said other end of said wire while said jaws are in engagement with said plate so that a tractive force can be established between said wire and said instrument by the engagement of said jaws with said plate.

8. The instrument of claim 7 in which said tightening means is uni-directional so that the tractive force remains imposed upon said wire during the deformation of the cross section of said other end thereof.

9. The instrument of claim 6 in which the outer ends of said jaws are slanted so that said jaws engage said plate in a manner to prevent the disengagement of said jaws from said plate during the imposition of the tractive load upon said wire by said tightening means.

10. The instrument of claim 6 in which said tightening means includes an indicator to signal visually the extent of the tractive load imposed upon the other end of said wire.

11. In an osteosynthesis method for maintaining the adjacent extremities of bone parts in a desired mutual position wherein a wire is utilized to impose a tractive load on plate means incorporating boreholes for the reception of said wire, said plate means being disposed in contiguity to said bone parts and said wire being utilized to impose its tractive effort on said bone parts through said plate means, the steps of: threading one end of said wire through one borehole in said plate means; deforming said end of said wire until said deformed portion is larger than said borehole; threading the other end of said wire through the other borehole in said plate means; impressing a tractive load on said wire by gripping the said other end of said wire extending through said other borehole; and, when the desired tractive force has been attained, deforming said other end of said wire until it is larger than the associated borehole to maintain said tractive force on the juxtaposed bone parts.

12. The method of claim 11 in which the deformation of the ends of said wires includes the scoring of said wires adjacent said deformed portions thereof to facilitate the severance of surplusage of said wires from said ends.

13. The method of claim 11 in which said tractive effort on said other end of said wire is maintained during the deformation of said other end.

14. The method of claim 13 in which, after the deformation of said other end of said wire, said tractive effort is increased upon said other end to sever the surplusage thereof from said other end of said wire.

15. The method of claim 11 in which said tractive force on said one and other ends of said wire is established by placing said tractive load on said one and other ends of said wire through the intermediary of said plate means.

* * * * *